United States Patent [19]

Brody et al.

[11] Patent Number: 5,955,063
[45] Date of Patent: Sep. 21, 1999

[54] WATER-BASED FINGERNAIL COATING

[76] Inventors: Donald E. Brody, 6078 Sunny Pointe Cir., Delray Beach, Fla. 33484; Carmine M. Zaccaria, 574 Chestnut St., Washington Township, N.J. 07075

[21] Appl. No.: 08/778,694

[22] Filed: Jan. 3, 1997

[51] Int. Cl.6 .............................. A61K 6/00; A61K 7/00; A61K 7/04
[52] U.S. Cl. ............................................. 424/61; 424/401
[58] Field of Search ..................... 424/401, 61; 252/364; 514/937

[56] References Cited

U.S. PATENT DOCUMENTS 4,897,261  1/1990  Yamazaki et al. ...................... 424/61

Primary Examiner—Thurman K. Page
Assistant Examiner—Sharon Howard

[57] ABSTRACT

A coating composition for cosmetic application on fingernails or toenails, characterized by containing 40 to 70% of water by weight, 15 to 35% of water-emulsion resin solids by weight, 0.1 to 2.0% of associative thickener solids by weight, 1 to 5% of an organic liquid, slower evaporating than water and soluble in water but not itself a solvent for the aforementioned water-emulsion resin solids, and 5 to 20% of an alcohol containing no more than 4 carbon atoms per molecule, all based on the total weight of composition.

5 Claims, No Drawings

WATER-BASED FINGERNAIL COATING

BACKGROUND OF THE INVENTION

1. Field of the Invention

The present invention concerns new and novel fingernail cosmetic coatings, more specifically water-based fingernail cosmetic coatings, which are unlike organic solvent-based fingernail cosmetic coatings in that a major part of the volatile content is water.

At the present time, commercial fingernail cosmetic coatings are generally of the organic solvent-based type, consisting primarily of a film-forming agent, such as nitrocellulose and alkyd or polyester resin, plus plasticizers and organic solvents. Although these organic solvent-based, fingernail cosmetic coatings have excellent film-forming properties, they also have serious drawbacks due to the inclusion of large amounts of organic solvents. These drawbacks include inflammability, very high Volatile Organic Content (5–7 pounds per gallon), strong and irritating solvent odor, and adverse effects on the human body, particularly on the nails and skin.

The Volatile Organic Content (VOC) of a coating is a measure of the total amount of organic solvent and other volatile substances which can be emitted to the atmosphere by the coating. It is expressed in units of pounds of volatile organic matter per gallon of coating, and, since water is an exempt solvent, for any given sample of coating it can be calculated by means of the following equation:

$$VOC = \frac{\text{pounds of total volatile matter} - \text{pounds of water contained}}{\text{gallons of total coating} - \text{gallons of water contained}}$$

2. Description of the Related Art

In order to overcome these drawbacks, aqueous fingernail coatings, in which the content of volatile organic compounds is considerably lower than in the organic solvent-based type, have been developed and disclosed. For example, Japanese Unexamined Patent Publications (Kokai) Nos. 54-28836 and 54-52736 and Japanese Examined Patent Publication (Kokoku) No. 55-43445 disclose aqueous fingernail coatings containing specified acrylic polymer emulsions, but coatings made according to these inventions are difficult to apply by brush and have poor film-forming ability, and the dried films have poor gloss and poor adhesion to fingernails. Japanese Unexamined Patent Publications (Kokai) Nos. 56-131513 and 57-56410 disclose aqueous fingernail coatings containing specified acrylic polymer microemulsions, but a drawback of the dry films from coatings made according to the latter two inventions is their extreme brittleness under mechanical wear, resulting in flaking or chipping of the films from the fingernails.

Yamazaki et al. (U.S. Pat. No. 4,897,261) discloses a fingernail cosmetic composition containing at least one resin and at least one organic solvent, characterized by incorporating therein water and a water-incorporating compound having at least one hydrophilic moiety, and, if desired, a moisturizing agent and a fragrance-containing agent. It is specified therein that the water-incorporating compound which may be used in the invention is, for example, a water-soluble polymer, an oil-soluble polymer, or a surface-active agent. However, it is clearly stated therein that, in the fingernail composition of the invention, water and the water-incorporating compound are incorporated as an internal phase of a water-in-oil emulsion, and, more particularly, the resins and organic solvents form a continuous external phase of an oil phase, and an aqueous phase is dispersed therein as the internal phase in the form of small particles (U.S. Pat. No. 4,897,261, Abstract, col.3, lines 29–35). Furthermore, Yamzaki et al. claims that the composition covered contains 0.5 to 30% of water based on the total weight of the composition (ibid., Claim No.1, col. 19, lines 42–45), and, in addition, they state, "A composition containing more than 30% by weight of water is not desirable" (ibid., Abstract, col. 3, lines 43–44).

The present invention does not fall under the claims or disclosures of U.S. Pat. No. 4,897,261 (Yamazaki et al.), as the latter includes only water-in-oil emulsions, whereas the present invention includes only resin-in-water emulsions, the resin corresponding to the "oil" or hydrophobic constituent of the Yamazaki et al. patent.

Furthermore, U.S. Pat. No. 4,897,261 encompasses only compositions containing 0.5 to 30% of water based on the total weight of the composition (Claim No. 1, col.19, lines 42–45, and Abstract, col. 3, lines 36–39), whereas compositions encompassed by application Ser. No. 08/778,694 contain 40–70% of water based on the total weight of the composition.

Yamazaki et al. does not teach specifically that the composition must contain a thickener, but some of the water-soluble and oil-soluble polymers which are listed therein may act as thickeners. However, none of the polymers which are cited therein are associative thickeners, while the inclusion of an associative type of thickener is essential in the composition taught by application Ser. No. 08/778,694. Associative thickeners are characterized by the fact that they have in their molecules hydrophobic (water-repellant) segments or blocks attached to the hydrophilic (water-attractive) segments. They thicken by means of a secondary valency association with other hydrophobic groups on other components of the composition, such as resins and pigments. The secondary valence association is broken when subjected to a high shearing stress, such as occurs during application of the composition by brushing. Associative thickeners, therefore, can provide effective thickening and anti-settling properties while the composition is at rest in a container, but permit good flow and leveling during application by brushing.

SUMMARY OF THE INVENTION

It has now been found that all of the above drawbacks and disadvantages can be remedied by the inclusion of certain specific ingredients in a 40–70% water-based coating composition.

Accordingly, an objective of the present invention is to provide a fingernail cosmetic, water-based coating composition having good film-forming ability and leveling, but equal in drying speed to commercial, organic solvent-based fingernail coatings.

A further objective of the present invention is to provide a fingernail cosmetic coating composition possessing all of the good properties listed above, and, in addition, having Volatile Organic Content of less than 3.0 pounds per gallon, far below the levels of present-day commercial, organic solvent-based fingernail coatings, which would result in much less organic solvent emission to pollute the atmosphere during manufacture and application.

A further objective of the present invention is to provide a fingernail cosmetic coating composition possessing all of the good properties listed above, and, in addition, giving dried films having good adhesion to fingernails, high gloss, and resistance to scratching, peeling and washing with water, soap or mild detergents.

A further objective of the present invention is to provide a fingernail cosmetic coating composition possessing all of the good properties listed above, and, in addition, having very mild and inoffensive odor.

A further objective of the present invention is to provide a fingernail cosmetic coating composition possessing all of the good properties listed above, and, in addition, being non-flammable.

A still further objective of the present invention is to provide a fingernail cosmetic coating composition possessing all of the good properties listed above, and, in addition, containing no toxic, carcinogenic or hazardous substances reportable under Section 313 of SARA TITLE III and 40 CFR Part 372.

All of these objectives have been attained by the art revealed in the present invention. In accordance with the present invention, there is provided a water-based, fingernail cosmetic composition which is equal to commercial, organic solvent-based fingernail coatings in brushability, drying speed, leveling, gloss, and performance in service, superior to the latter in resistance of the dry films to chipping and peeling, and, in addition, which has Volatile Organic Content (VOC) of less than 3.0 pounds per gallon, is non-inflammable, has very mild, non-irritating odor, and contains no reportable quantities of toxic, carcinogenic or hazardous chemical subject to the reporting requirements Section 313 of SARA TITLE III Emergency Planning and Community Right-To-Know Act of 1986 and of 40 CFR Part 372.

DESCRIPTION OF THE PREFERRED EMBODIMENTS

The term "fingernail coatings" used herein encompasses fingernail lacquers, fingernail enamels, fingernail enamel base coats, fingernail enamel overcoats, fingernail strengthening coats, and the like. Popularly they are often called "fingernail polishes".

The term "fingernail cosmetic composition" used herein means make-up cosmetics applied to a fingernail or toenail for protection and/or beautification thereof.

Good adhesion to fingernails, high gloss, hardness, film strength and resistance of applied films, when completely dry, to water, soap or mild detergents was achieved by the utilization of 20 to 35% of solids, by weight, of a selected type of water-emulsion resin. Examples of such resins include, but are not limited to, an acrylic copolymer, a styreneacrylic copolymer, a polyurethane-acrylic mixture or copolymer, or a mixture or combination of any these.

Speed of drying was achieved by the incorporation of 5 to 20%, by weight, of an alkanol (alcohol) containing no more than four carbon atoms per molecule. Examples of such alcohols include, but are not limited to, ethanol (commonly called ethyl alcohol), 1-propanol (commonly called normal propyl alcohol), 2-propanol (commonly called isopropyl alcohol), 1-butanol (commonly called normal butyl alcohol), and 2-butanol (commonly called secondary butyl alcohol).

Sufficient wet time (which means the time that the applied film remains liquid and thin enough to brush easily and still level well) was achieved by the inclusion of 1 to 5%, by weight of the total coating, of an organic liquid, slower evaporating than water, and soluble in water, but not by itself a solvent for the aforementioned water-emulsion resin. Substances suitable for this purpose include, but are not limited to, propylene glycol and ethylene glycol.

Good flow and leveling, along with minimization of pigment settling and the proper viscosity and rheology for good brushability and film build, was achieved by the inclusion of 0.1 to 2.0%, by weight of the total coating, of an associative thickener, such as a hydrophobically-modified, alkali-solution emulsion (HASE) or a hydrophobically-modified, ethylene oxide-urethane block copolymer (HEUR). Optionally, a variety of surface-active agents and/or defoamers may be included, and a water-emulsified wax for increased mar resistance.

Aqueous pigment dispersions available in a compatible vehicle, or, alternatively, dry pigment powders dispersed in water plus suitable surface-active agents, may be mixed with the composition taught by the present invention in various proportions to produce colored, metallic, irridescent, fluorescent, pearlescent, fiber-reinforced fingernail-strengthening or high-build ridge-filling coatings.

EXAMPLES

The following examples are intended to illustrate the present invention and in no way limit the scope thereof. In all of the examples the percentages are given as percent by weight, unless otherwise specified.

TABLE 1

COMPOSITION OF UNPIGMENTED EXAMPLES
(% by weight)

| Ingredients | Ex.1 31A | Ex.2 40A | Ex.3 58B | Ex.4 58F | Ex.5 58C | Ex.6 58G | Ex.7 59F | Ex.8 63A |
|---|---|---|---|---|---|---|---|---|
| Styrene-acrylic copolymer emulsion, 42% NV (Note 2) | 70.0 | 70.0 | — | — | — | — | — | — |
| Purely acrylic copolymer emulsion, 36% NV (Note 2) | — | — | 85.4 | 81.9 | 85.1 | 81.3 | 80.9 | 80.9 |
| Ethylene glycol, tech.grade | 1.08 | — | — | — | — | — | — | — |
| Propylene glycol, tech.grd. | — | 2.08 | 2.17 | 2.09 | 2.16 | 2,07 | 2.97 | 2.97 |
| Isopropyl alcohol, tech.grd. | 7.50 | 7.52 | 4.73 | 8.54 | 4.71 | 8.49 | 8.48 | 8.48 |
| Aqua ammonia, 29% $NH_3$ | 0.16 | 0.10 | 0.10 | 0.10 | 0.10 | 0.10 | 0.10 | 0.10 |
| Non-ionic surfactant, 50% NV in alcohol | 0.32 | 0.30 | 0.33 | 0.33 | 0.34 | 0.33 | 0.33 | 0.33 |
| Silicone wetting agent, 12.5% NV | — | — | 0.50 | 0.50 | 0.52 | 0.50 | 0.50 | 0.50 |
| Defoamer, 100% NV | 0.10 | 0.10 | 0.10 | 0.10 | 0.10 | 0.10 | 0.10 | 0.10 |
| Dipropylene glycol methyl ether (DPGME) | 4.30 | — | — | — | — | — | — | — |

TABLE 1-continued

COMPOSITION OF UNPIGMENTED EXAMPLES
(% by weight)

| Ingredients | Ex.1 31A | Ex.2 40A | Ex.3 58B | Ex.4 58F | Ex.5 58C | Ex.6 58G | Ex.7 59F | Ex.8 63A |
|---|---|---|---|---|---|---|---|---|
| Dipropylene glycol propyl ether (DPGPE) | — | 3.00 | 3.13 | 3.01 | 3.12 | 2.99 | 2.97 | — |
| Dibutylene glycol methyl ether (DBGME) | — | — | — | — | — | — | — | 2.97 |
| Carnauba wax emulsion, 25% NV (Note 3) | 2.80 | — | — | — | — | — | — | — |
| Polyethylene wax emulsion 25% NV (Note 4) | — | 2.80 | 2.92 | 2.81 | 2,91 | 2.79 | 2.77 | 2.77 |
| Associative thickener, 35% NV (Note 5) | 0.84 | 0.80 | 0.65 | 0.62 | — | — | 0.88 | 0.88 |
| Associative thickener, 17.5% NV (Note 6) | — | — | — | — | 0.94 | 1.33 | — | — |
| Water | 12.9 | 13.3 | — | — | — | — | — | — |

Note 1: Rhoplex WL-96, from Rohm and Haas Co., Philadelphia. Pa.
Note 2: Chempol 20-4301, from CCP Polymers, N>Kansas City, Mo.
Note 3: MichemLube 110, from Michelman, Inc., Cincinnati, Ohio.
Note 4: Jonwax 26, from S C Johnson Polymer, Racine, Wis.
Note 5: Acrysol RM-8, from Rohm and Haas Co., Philadelphia, Pa.
Note 6: Acrysol SCT-275, from Rohm and Haas Co., Philadephia, Pa.

Unpigmented Examples

In Table 1, above, and all of the following tables, Ex. is used as an abbreviation for Example Number. Each Ex. is followed on the next line by the inventor's own reference number for the particular example. The word emulsion means a fine particle size, stable dispersion of the polymer or resin in water. The symbol NV stands for non-volatile content by weight, cps for centipoises, and RPM for revolutions per minute (of the viscometer spindle).

Eight unpigmented examples of the composition taught by the present invention were prepared from the ingredients listed in Table 1, above. Each example was prepared by adding the ingredients in the order listed, with continuous stirring by a high-speed laboratory mixer until the mixture was homogeneous. Properties and performance of each example are shown in Table 2.

The pH was determined using Hydrion Test Papers. It represents the degree of acidity or alkalinity of the composition, and a value of 7.0 indicates neutrality. However, most water-emulsion resins and the coatings made with them are most stable when buffered to a pH range of 7.5 to 8.0, at which they are very mildly alkaline and not harmful to human skin or nails on external contact. Aqua ammonia (a solution of ammonia in water) is the preferred buffering agent.

Viscosity was measured using a Brookfield RVT viscometer equipped with a #3 spindle, after bringing the sample to the standard temperature of 77 degrees F. In order to attain equilibrium shear rate conditions at each speed, the spindle was run at a speed of 20 RPM for three minutes before taking the first reading, then at 50 RPM for three minutes before taking the second reading. The ratio of the viscosity in centipoises at a speed of 20 RPM to the viscosity in centipoises at a speed of 50 RPM is here called the thixotropic index, and the latter is a measure of the susceptibility of the viscosity to reduction by shearing. It is known in the fingernail cosmetic coating industry that, if the thisotropic index, or a similar measure under any other name, is too low, the coating will not flow or level well when applied by brushing (which generates a high degree of shearing) unless the low shear rate viscosity is very low, in which case the coating will probably run and sag during application, and in storage will tend to separate and settle any pigments dispersed in it. Conversely, if the thixotropic index is too high, the coating will probably run and sag during application, unless the low shear rate viscosity is very high, in which case the coating will not flow and level well. The thixotropic index value of 1.3 to 1.4 achieved by the composition of the present invention, as attested by the values obtained from the samples, is ideal for maintaining good flow and leveling consistent with freedom from sagging and settling, and is attributable to the employment of an associative thickener.

Total non-volatile content was calculated as the sum of the non-volatile content of each ingredient multiplied by the percent by weight of that ingredient in the composition.

Volatile organic content (VOC) was calculated using the equation shown in Background of the Invention, Section 1. Field of the Invention.

Storage stability was evaluated by filling a four fluid ounce, tall-form glass jar with the sample, capping the jar tightly and placing it for 14 days in an electric oven maintained at 120 degrees F., then inspecting the contents of the jar for evidence of layer separation, gelation, curdling, or excessive change in viscosity, brushability, color or hiding power. Keeping a sample at 120° F. for 14 days is considered to have an effect similar to storage at ordinary room temperature for two years. Symbols employed for the stability ratings are as follows:

N=no change, L=layering, G=gelation or curdling, V=viscosity change, O=odor change, B=brushability change, C=color change, H=hiding chg.

None of the samples tested showed any of these changes after two weeks storage at 120° F. All had been prepared in accordance with the teaching of the present invention.

A sample of each example was filled into conventional one fluid ounce fingernail polish bottles, and, using the small brush provided therein, brushed out, in turn, onto six synthetic simulated fingernails made of nylon plastic, and also on the fingernails of several human volunteers.

The time in minutes required for the films of each sample to dry free from tackiness was measured using a stopwatch. Tackiness was tested by pressing a piece of tissue paper against the surface of the film with a thumb for 60 seconds, applying as much pressure as possible, then listening as the paper was pulled sharply away from the surface. If no tearing sound was heard the film was judged to be free from tackiness. The time required for the films applied on human fingernails to dry was in every case less than that for the same sample applied on the nylon fingernails, indicating that there was some diffusion of the volatile liquids through the human fingernails. However, as no hazardous, toxic or carcinogenic substances reportable under Section 313 of SARA TITLE III and of 49 CFR Part 372 are contained in coatings which are prepared according to the teaching of the present invention, this needs cause no concern.

Brushability was assessed from the ease with which the liquid coating could be spread over the entire surface of the synthetic fingernail to provide adequate film build before the wet film became so viscous that it could no longer be spread.

Leveling was rated from visual inspection of the dry film for striations.

Applied on the nylon fingernails, the dry films from each of the samples remained tender and easy to scrape off for several hours after becoming free from tackiness, but within 24 hours they became quite hard and resistant to scratching, scraping or peeling. The time span for these events was considerably shorter when the same samples were applied on human fingernails, probably also attributable to diffusion of some of the remaining volatiles through the nails. On the human nails the films were more adherent and less easy to peel off from the time they became free from tackiness, probably due to higher mechanical adhesion resulting from anchoring into the porosity of the human nails. During many weeks of wear, these films were found to be more adherent and less prone to chipping or peeling then the dry films from several commercial, organic solvent based fingernail cosmetic coatings, which the authors evaluated by applying and wearing at the same time, on some of the fingers of the same hands, as those on which the samples of the present invention were applied and worn.

From an hour after application on, and during several weeks of routine wear, the dry films from the samples of the present invention resisted routine washing with warm water plus soap or customary hand-washing detergents as well as, or better than, the films from the commercial, organic solvent-based fingernail cosmetic coatings. The former either eventually failed from normal abrasion and wear-and-tear, or else the wearers became tired of their appearance or color and decided to remove them. Although they were resistant to removal with ethyl acetate alone, or ethyl acetate plus toluene or xylene (the constituents of most commercial fingernail polish removers prior to the recent restrictions on the use of aromatic hydrocarbons in the Clean Air Act amendments), they could be removed, when desired, by rubbing with tissue paper, paper napkins or cloth, wet with various commercial fingernail polish removers (most of which not contain acetone as well as ethyl acetate), or wet with aqueous compositions containing at least 50% of N-methyl pyrrolidone.

TABLE 2

PROPERTIES AND PERFORMANCE OF UNPIGMENTED EXAMPLES FROM TABLE 1

|  | Ex.1 31A | Ex.2 40A | Ex.3 58B | Ex,4 58F | Ex.5 58C | Ex.6 58G | Ex.7 59F | Ex.8 63A |
|---|---|---|---|---|---|---|---|---|
| Properties |  |  |  |  |  |  |  |  |
| pH | 9 | 7.5 | 7.5 | 7.5 | 8 | 8 | 7.5 | 7.5 |
| Viscosity at 20 RPM, cps. | 1270 | 1625 | 1740 | 1080 | 1175 | 1400 | 1550 | 2645 |
| Viscosity at 50 RPM, cps. | 954 | 1230 | 1342 | 838 | 870 | 1000 | 1168 | 1958 |
| Thixotropic Index | 1.33 | 1.32 | 1.30 | 1.29 | 1.35 | 1.40 | 1.33 | 1.35 |
| Total NV, % by weight | 30.2 | 30.2 | 31.4 | 30.2 | 31.4 | 30.2 | 30.1 | 30.1 |
| VOC, pounds per gallon | 2.2 | 2.2 | 2.3 | 2.6 | 2.3 | 2.6 | 2.7 | 2.7 |
| Stability, 14 days at 120° F. | N | N | N | N | N | N | N | N |
| Applied on nylon nails: |  |  |  |  |  |  |  |  |
| Time to dry, minutes | 5 | 5 | 5 | 10 | 5 | 10 | 10 | 10 |
| Brushability | G | VG | F | G | G | VG | E | E |
| Leveling (film smoothness) | VG | E | F | VG | E | E | E | E |
| Gloss of dry film | E | E | E | E | E | E | E | E |
| Adhesion (peel resistance) | E | E | E | E | E | E | E | E |
| Applied on human nails: |  |  |  |  |  |  |  |  |
| Time to dry, minutes | 3 | 3 | 3 | 5 | 3 | 5 | 5 | 5 |
| Leveling (film smoothness) | G | VG | F | G | G | VG | E | E |
| Adhesion (peel resistance) | E | E | E | E | E | E | E | E |
| Resistance to washing | E | E | E | E | E | E | E | E |

Symbols employed in the tables for the ratings of brushability, leveling, gloss of the dry film, adhesion and resistance to washing are as follows: E=excellent, VG=very good, G=good, F=fair, P=poor. It may be noted that all of the examples of the present invention performed extremely well in all of these tests, with the exception of brushability and leveling, in which these was considerable variation at first, primarily due to differences in the solvent balance of the samples. As the research progressed, however, ways were found to fine tune the composition so as to eliminate this deficiency.

Pigmented Versions

As noted above, pigments can be incorporated into the water-based fingernail cosmetic coating of the present invention in order to produce colored, metallic, pearlescent, iridescent, nail strengthening (fiber-reinforced), or ridge-filling coatings. Following are examples of the composition of some of these products.

TABLE 3

COMPOSITION AND PROPERTIES OF PIGMENTED VERSIONS

Example 9
52D
SCARLET RED WATER-BASED
FINGERNAIL COATING

| Ingredient | % by Wt. |
|---|---|
| Water | 15.8 |
| Aqua ammonia, 29% $NH_3$ | 0.2 |
| Anionic surfactant, 96% NV | 2.4 |
| Propylene glycol | 0.8 |
| D&C Red #6, Barium Lake | 7.9 |
| -Disperse at high speed. Then add:- | 71.3 |
| Clear, water-based fingernail coating #59F (Example 7) | |
| Total | 100.0 |
| Properties | |
| pH | 7.5 |
| Viscosity at 20 RPM, cps. | 1360 |
| Viscosity at 50 RPM, cps. | 1104 |
| Thixotropic index | 1.23 |
| Total non-volatile content | 2.5% |
| Applied on nylon fingernails: | |
| Brushability | E |
| Leveling (film smoothness) | E |
| Gloss of dry film | E |
| Adhesion | E |
| Color | Glossy, translucent scarlet |

Example 10
60L
FRENCH WHITE WATER-BASED
FINGERNAIL COATING

| Ingredient | % by Wt. |
|---|---|
| Liquaflex WD9035* (dispersion of $TiO_2$ in water-reducible resin | 8.0 |
| Clear, water-based fingernail coating #59F (Example 7) | 91.2 |
| Defoamer, 100% NV | 0.1 |
| Associative thickener, HEUR type, 35% NV | 0.7 |
| -Mix at high speed for 10 minutes- | |
| Total | 100.0 |
| Properties | |
| pH | 7.5 |
| Viscosity at 20 RPM, cps. | 1715 |
| Viscosity at 50 RPM, cps. | 1298 |
| Thixotropic index | 1,32 |
| Total non-volatile content | 31.6% |
| Applied on nylon fingernails: | |
| Brushability | E |
| Leveling (film smoothness) | E |
| Gloss of dry film | E |
| Adhesion | E |
| Color | Very glossy, opaque white |

TABLE 3-continued

COMPOSITION AND PROPERTIES OF PIGMENTED VERSIONS

Example 11
59H
WATER-BASED FINGERNAIL
FORTIFIER AND PRIMER

| Ingredient | % by wt. |
|---|---|
| Clear, water-based fingernail coating #59F (Example 7) | 96.3 |
| Anionic grind-aid, 100% NV | 0.5 |
| Defoamer, 100% NV | 0,1 |
| -Sift in under strong agitation:- | |
| Adhesion promoter, 47% NV | 2.1 |
| Pyrogenic silica powder | 1.0 |
| Mix 10 min. under strong agitation | |
| Viscosity at 20 RPM, cps. | 2250 |
| Viscosity at 50 RPM, cps. | 1500 |
| Thixotropic index | 1.50 |
| Applied on nylon fingernails: | |
| Time to dry, minutes | 10 |
| Adhesion | E |
| Film color | Matte, translucent |

Example 12
60K
WATER-BASED FINGERNAIL
RIDGE FILLER

| Ingredient | % by wt. |
|---|---|
| Clear, water-based fingernail coating #59F (Example 7) | 99.1 |
| Non-ionic grind-aid | 0.3 |
| Defoamer, 100% NV | 0.1 |
| -Sift in under strong agitation:- | |
| Nylon floc 1 and ½ denier x 0.30" | 0.5 |
| Mix 10 min. under strong agitation | |
| Viscosity at 20 RPM, cps. | 2265 |
| Viscosity at 50 RPM,cps. | 1468 |
| Thixotropic index | 1.54 |
| Applied on nylon fingernails: | |
| Time to dry, minutes | 10 |
| Film build | E |
| Film color | Clear, colorless |

We claim:

1. A water-based cosmetic coating composition, for application on fingernails or toenails, consisting essentially of the following ingredients by weight based on the total weight of the composition:

40–70% of tap water or deionized water,

5–20% of methanol, ethanol, 1-propanol, 2-propanol, 1-butanol or 2-butanol,

15–35% of the water-emulsion resin or polymer solids, acrylic copolymer, styrene-acrylic copolymer, urethane-acrylic copolymer, or mixtures thereof, 0–10% of an organic liquid, which is the methyl ether of dibutylene glycol, the propyl ether of dipropylene glycol or the butyl ether of dipropylene glycol, 1–5% of an organic liquid, which is slower evaporating than water, and is soluble in water, but is not soluble in the resinous binder of the coating, ethylene glycol or propylene glycol, 0.1–2.0% of the associative thickener solids, a hydrophobically-modified, alkali-soluble emulsion or a hydrophobically modified ethylene oxide-urethane block copolymer.

2. The coating composition according to claim 1 wherein the volatile organic content is less than 3.0 pounds per gallon.

3. The coating composition according to claim 1 which is non inflammable.

4. The coating composition according to claim 1 which has an inoffensive, non-pungent odor.

5. The coating composition according to claim 1 which contains no reportable quantities of toxic, carcinogenic or hazardous substance.

* * * * *